United States Patent [19]

Neuber et al.

[11] Patent Number: 5,227,529
[45] Date of Patent: Jul. 13, 1993

[54] PROCESS FOR THE ACYLATION OF NAPHTHYL ETHERS WITH THE AID OF ZEOLITE CATALYSTS

[75] Inventors: Marita Neuber, Frankfurt am Main; Ernst I. Leupold, Neu-Ansbach, both of Fed. Rep. of Germany

[73] Assignee: Hoechst Aktiengesellschaft, Frankfurt am Main, Fed. Rep. of Germany

[21] Appl. No.: 944,798

[22] Filed: Sep. 14, 1992

Related U.S. Application Data

[63] Continuation of Ser. No. 707,466, May 30, 1991, abandoned.

[30] Foreign Application Priority Data

Jun. 1, 1990 [DE] Fed. Rep. of Germany ....... 4017681

[51] Int. Cl.⁵ ............................................. C07C 45/00
[52] U.S. Cl. .................................... 568/319; 568/322
[58] Field of Search ................................ 568/319, 322

[56] References Cited

U.S. PATENT DOCUMENTS

| | | | |
|---|---|---|---|
| 4,304,941 | 12/1981 | Lee et al. | 568/319 |
| 4,593,125 | 6/1986 | Davenport et al. | 568/322 |
| 4,652,683 | 3/1987 | Nicolau et al. | 568/319 |
| 4,714,781 | 12/1987 | Gupta | 568/319 |
| 4,835,319 | 5/1989 | Corbin et al. | 568/322 |
| 4,868,338 | 9/1989 | Magni et al. | 568/322 |
| 4,960,943 | 10/1990 | Batta et al. | 568/319 |

FOREIGN PATENT DOCUMENTS

| | | | |
|---|---|---|---|
| 0279322 | 8/1988 | European Pat. Off. | 568/322 |
| 0282134 | 9/1988 | European Pat. Off. | 568/319 |
| 0334096 | 9/1989 | European Pat. Off. | 568/319 |

OTHER PUBLICATIONS

Olah, "Friedel-Crafts & Related Reactions", vol. III, pp. 64-7 and 72-73 (1964).
Chiche et al., Appl. Catal., vol. 30, pp. 365-9 (1987).

Primary Examiner—James H. Reamer
Attorney, Agent, or Firm—Connolly and Hutz

[57] ABSTRACT

A process for the acylation of naphthyl ethers of the formula

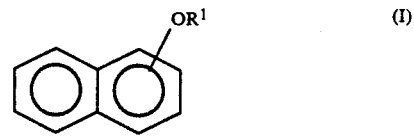

using acylating agents of the formula $R^2$—CO—X to give acylated naphthyl ethers of the formula

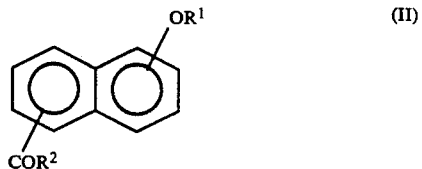

in which $R^1$ and $R^2$ independently of one another are $C_1$— to $C_{10}$-alkyl, $C_2$— to $C_{10}$-alkenyl or $C_3$- to $C_8$-cycloalkyl and $R^2$ is additionally $C_6$- to $C_{10}$-aryl and X is Cl, Br, —$OCOR^2$, OH or $C_1$- to $C_3$-alkoxy, comprises carrying out the reaction presence of zeolite catalysts which have the formula $Z \cdot Al_2O_3 \cdot x\, SiO_2$ (III) in the anhydrous and template-free form, in which Z is $M^I_2O$, $M^{II}O$ and/or $(M^{III})_2O_3$, in which $M^I$ is an alkali metal atom, ammonium or a hydrogen atom, $M^{II}$ is an alkaline earth metal atom and $M^{III}$ is a rare earth metal of atomic number 57 to 71 in the periodic table of the elements, and x is a number from 4 to 4000, with the proviso that at least 50% of the negative lattice charges are compensated by protons, ammonium and/or the other metal ions mentioned under $M^{II}$ and $M^{III}$, and the pores of which are formed from at least 10 tetrahedral atoms.

15 Claims, No Drawings

PROCESS FOR THE ACYLATION OF NAPHTHYL ETHERS WITH THE AID OF ZEOLITE CATALYSTS

This is a continuation of Ser. No. 07/707,466, filed May 30, 1991, now abandoned.

DESCRIPTION

The present invention relates to a process for the acylation of naphthyl ethers with the aid of zeolite catalysts. The products, in particular 2-acetyl-6-methoxynaphthalene, are important intermediates for the preparation of pharmaceuticals or of monomers for polyesters.

It is known to acylate naphthyl ethers, such as methoxynaphthalene, with the aid of Lewis acids, such as $AlCl_3$, as catalysts. In this process, a 1-naphthyl ether is acylated in the 4-position; with 2-naphthyl ethers the position of acylation depends strongly on the choice of solvent: if the reaction is carried out, for example, in carbon disulfide, 1-acyl-2-alkoxynaphthalene is the main product. If, on the other hand, the reaction is carried out, for example, in nitrobenzene, mainly 6-acyl-2-alkoxynaphthalene is formed (Houben-Weyl, Methoden der Organischen Chemie (Methods of Organic Chemistry), 4th edition, Volume VII/2a, p. 71/73 (1973)). 2-Naphthyl ethers can be reacted in anhydrous hydrofluoric acid with high selectivity to give the products acylated in the 6-position (U.S. Pat. No. 4,593,125).

These processes, however, have a number of disadvantages. Thus, the Lewis acid catalysts must be employed in at least stoichiometric amounts in order that the acylation reaction can take place. During the working-up of the reaction products, the catalyst is destroyed, inorganic salts being formed. In all cases the reaction must be carried out using solvents. In the case of acylation in anhydrous hydrofluoric acid, the catalyst is simultaneously the solvent. After separating from the reaction product, the hydrofluoric acid can be re-used. The acylated products must be neutralized, salts likewise being obtained. Moreover, anhydrous hydrofluoric acid is extremely toxic and corrosive. Industrially expensive equipment made from special materials is necessary in order to be able to work with hydrofluoric acid.

There was therefore a need for an improved process for the acylation of naphthyl ethers, which is distinguished in particular in that it is simple to operate, and can be carried out in media which are not corrosive and/or toxic and also without solvents. Moreover, the catalyst should be simple to separate and reusable.

It has now been found that naphthyl ethers of the formula I

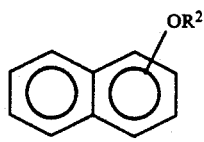

can be reacted with acylating agents of the formula $R^2$—CO—X to give acylated naphthyl ethers of the formula II

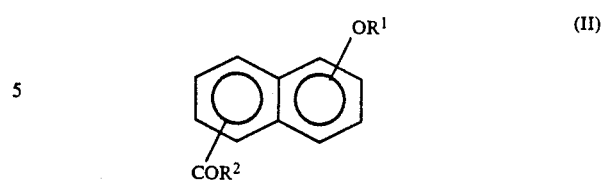

in which $R^1$ and $R^2$ independently of one another are $C_1$- to $C_{10}$-alkyl, $C_2$- to $C_{10}$-alkenyl or $C_3$- to $C_8$-cycloalkyl and $R^2$ is additionally $C_6$- to $C_{10}$-aryl and X is Cl, Br, $OCOR^2$, OH or $C_1$- to $C_3$-alkoxy, by employing zeolites as catalysts which have the formula $Z.Al_2O_3.x\ SiO_2$ (III) in the anhydrous and template-free form, in which Z is $M^I_2O$, $M^{II}O$ and/or $(M^{III})_2O_3$, in which M is an alkali metal, ammonium or hydrogen, $M^{II}$ is an alkaline earth metal and $M^{III}$ is a rare earth metal of atomic number 57 to 71 in the periodic table of the elements, preferably cerium or lanthanum, and x is an integer from 4 to 4000, with the proviso that at least 50% of the negative lattice charges are compensated by protons, ammonium and/or the other metal ions mentioned under $M^{II}$ and $M^{III}$, and the pores of which are formed from at least 10 tetrahedral atoms.

It is admittedly known that phenyl ethers, such as anisole, can be acylated with the aid of zeolites as catalysts, it being possible to achieve conversions up to 75% and selectivities for 4-alkoxyphenyl ketones of 98 to 100% (German Offenlegungsschrift 3,809,260). Nevertheless, according to the prior art it was not to be expected that, in comparison to the phenyl ethers, the very much more bulky naphthyl ethers could also be acylated using zeolites as catalysts. According to Weisz (Pure Appl. Chem. 52, 2091-2103 (1980)), in the range of configuration diffusion (i.e. diffusing molecules and pore widths have comparable dimensions), the diffusion coefficient of two molecules can differ by several orders of magnitude if the dimensions of the molecules are only insignificantly different (for example the effective diffusion coefficient of o- and p-xylene in the zeolite ZSM-5 differs by the factor $10^4$, Weisz, loc. cit.). The diffusion coefficient depends on the temperature. This dependence can be described by an equation analogous to the Arrhenius equation. The activation energy for the diffusion is in this case all the greater, the better the dimensions of molecules and pore widths agree (Weisz, loc. cit). According to this knowledge, it was to be expected that the bulky naphthyl ethers and the still bulkier acylated reaction products would only be able to diffuse into the zeolite pores sufficiently rapidly at very high temperatures, if at all, in order to obtain satisfactory conversions and yields.

Surprisingly, however, naphthyl ethers can already be reacted at low reaction temperatures. Thus, for example, the reaction of 2-methoxynaphthalene with acetic anhydride at 120° C. in the liquid phase gave a yield of 20.0% of acetylmethoxynaphthalenes with a selectivity of 98%.

It has additionally been found that when employing 2-naphthyl ethers, the proportions of the two products principally formed, namely the 2-naphthyl ethers acylated in the 1- or 6-position, can be changed by variation of the experimental conditions and of the acylating agent. Thus, the acylation preferably takes place in the 1-position if the reaction is carried out with acid chlorides, and in the 6-position if carboxylic acids or carboxylic acid/carboxylic anhydride mixtures are employed.

The acylation reaction can be carried out both in the gas phase and in the liquid phase. The liquid phase reaction is preferred in this case. When working in the liquid phase, the proportion of the naphthyl ether acylated in the 6-position is increased if the acylating agent is added slowly and is not present in the reaction mixture from the start. Results according to these different process variants are contained in the examples.

When working in the gas phase, an increased reaction temperature also leads to increased formation of the 6-acyl-2-alkoxynaphthalene. Some results for this are also given in the examples.

The reaction proceeds very selectively in the liquid phase. In the gas phase, on the other hand, isomerization of alkoxynaphthalenes to alkylnaphthols, disproportionation of alkoxynaphthalenes, hydrolytic cleavage of the reactants and the formation of naphthyl esters takes place to a certain extent. At higher temperatures, reactions of the carboxylic acid derivatives can also take place in the gas phase reactions.

Examples of suitable $R^1$ and $R^2$ radicals are methyl, ethyl, propyl, isopropyl, butyl, isobutyl, the isomeric amyls, hexyls, octyls, nonyls, decyls, and also vinyl, propenyl, butenyl, the isomeric amylenes, hexenes, octenes and decenes.

Examples of specific naphthyl ethers (I) for the process according to the invention are 1- and 2-methoxynaphthalene, 1- and 2-ethoxynaphthalene, 1- and 2-propoxynaphthalene, cyclohexyl 1-naphthyl ether and cyclohexyl 2-naphthyl ether.

Examples of acylating agents for the process according to the invention are acetic acid, acetic anhydride, acetyl chloride, acetyl bromide, methyl acetate, propionic acid, propionic anhydride, propionyl chloride, butyric acid, butyric anhydride, butyryl chloride, isobutyric acid, isobutyric anhydride, isobutyryl chloride, pivaloyl chloride, pivalic anhydride, valeric acid, valeryl chloride and valeric anhydride. Carboxylic anhydrides or mixtures of carboxylic acids and their anhydrides are preferred here.

Suitable catalysts for the process according to the invention are zeolites as defined in formula (III), whose pore openings are formed from at least 10 tetrahedral atoms. Si and Al are designated as tetrahedral atoms which are surrounded tetrahedrally by oxygen atoms. These tetrahedra are linked via common oxygen atoms and form a crystal structure which is penetrated by defined pores and cavities. The pore widths and shapes depend on the type of zeolite (see, for example, Atlas of Zeolite Structure Types, W. M. Meier and D. H. Olson, 1987).

However, zeolites are also suitable in which a part of the aluminum or silicon is replaced by other lattice atoms, preferably boron, iron, gallium, germanium, titanium and/or zirconium.

The negative charges of the AlO. tetrahedra are compensated by exchangeable cations such as, for example, $H^+$, $Na^+$, $K^+$, $Ca^{2+}$, $Mg^{2+}$ or organic cations such as $N^+R_4$ and $P^+R_4$.

Zeolites suitable for the process according to the invention are, for example, the zeolites ZSM-5 (U.S. Pat. No. 3,702,886), ZSM-11 (U.S. Pat. No. 3,709,979), ZSM-12 (U.S. Pat. No. 3,970,544), ZSM-20 (U.S. Pat. No. 3,972,983), beta (U.S. Pat. No. 3,308,069), EU-1 (European Patent 042,226), Y, L, offretite or mordenite (described in D. W. Breck, "Zeolite Molecular Sieves", 1974).

Molecular sieves based on aluminum phosphate, in which a part of the tetrahedral atoms is replaced, for example, by Si, Co, Mg and/or Mn, can additionally be used.

Said zeolites can be prepared by hydrothermal synthesis according to procedures from the literature. After crystallization, the zeolites are filtered off, dried and calcined in an oxidizing atmosphere, preferably in air, in order to remove the organic template from the pores. (The template-free form is free of alkylammonium or -phosphonium ions and of amines). Alkali metal ions which may be present (in this case Z in formula (III) is $M_2O$) are then exchanged for di- or trivalent ions of the monium ions or protons by ion exchange. Ion exchange with $NH_4^+$ or $H^+$ is very particularly preferred here. This acidic modification is necessary as the zeolite does not otherwise display any catalytic effect. It is expedient here that at least 50%, preferably at least 75%, of the alkali metal ions are replaced by the other ions mentioned. At 200° to 800° C., preferably at 400° to 550° C., the zeolites are converted into the catalytically active form by dehydration (and deammonation in the case of $NH_4^+$ forms). The $SiO_2/Al_2O_3$ ratio of the zeolites can vary within a wide range, for example between 4 and 4000—depending on the type of zeolite. The aluminum content of the zeolites used according to the invention can be reduced within the limits mentioned by treatment with mineral acids, organic acids or chelating substances for the purposes of a continuing modification. $SiO_2/Al_2O_3$ ratios between 20 and 300 are preferred. The crystallite size can be, for example, between about 0.01 and about 10 μm, preferably between about 0.05 and about 0.1 μm.

For use according to the invention, the zeolites are advantageously brought into a suitable application form, for example into extrudate form, with the aid of binders. Suitable binders are in particular oxides, hydroxides or hydroxychlorides of aluminum and the oxides of silicon, titanium and zirconium and also clay materials.

The acylating agent can be employed, for example, in a ratio of 0.1 to 20 mol, preferably of 0.5 to 5 mol, per mol of naphthyl ether. The reaction temperatures can be between about 30° and 500° C., preferably between 100° and 300° C. It is favorable here, for the liquid phase acylation, to choose temperatures in the lower range between about 30° and about 200° C., preferably between 120° and 170° C., and, for the gas phase acylation, to use temperatures in the upper temperature range between about 150° and 500° C., preferably between 200° and 300° C.

The pressure has little effect on the course of the reaction. It can be adjusted to values between 0.5 and 100 bar, preferably between 1 and 10 bar. Most favorably, the reaction is carried out at atmospheric pressure. For reaction in the liquid phase, to achieve a reaction temperature which is higher than the boiling temperature of the reaction mixture, it may be necessary to work under pressure.

The acylation in the liquid phase can be carried out in all suitable equipment, most simply in a stirred vessel using pulverulent, suspended catalyst.

The reactants can in this case be brought to the reaction temperature together with the catalyst. In certain cases it is more favorable to add one of the reaction components, preferably the acylating agent, slowly after reaching the reaction temperature. The reaction can be carried out in the absence or in the presence of solvents such as nitrobenzene which are inert to the reactants and catalysts.

Relative to the weight of reactants employed, it is favorable to employ between 0.5 and 100% by weight of catalyst, preferably between about 1 and 10% by weight. The reaction period can be between about 0.5 h and several days, preferably between 2 and 10 hours. After reaction in the liquid phase has been carried out, the zeolite can be removed from the reaction mixture by filtration in a simple manner.

In principle, all equipment suitable for gas phase reactions can be used for carrying out the reaction in the gas phase. A solid-bed flow reactor is simplest to operate industrially. The catalyst can in this case be incorporated in the reactor in the form of pellets. To prepare the pellets, the zeolite can be compressed together with a binder material such as $Al_2O_3$ or $SiO_2$ or else in binder-free form.

The reactants can be metered into the reactor in liquid form, it being possible for a naphthyl ether which is solid at room temperature to be melted or dissolved in an inert solvent or in an excess of acylating agent. If it is wished to work in the gas phase, the reactants are evaporated upstream of the catalyst bed. They can also be converted into the gas phase by suitable measures upstream of the reactor and then passed over the catalyst. In this case, the reactants can be employed on their own or mixed with a gas which is inert with respect to the reaction, such as nitrogen or hydrogen. The products are condensed downstream of the reactor.

The residence time of the reactants can be between about 0.05 and 20 s, preferably between 1 and 10 s. The space velocities (LHSV=liquid hourly space velocity) can be adjusted in the range from 0.1 to 5 $h^{-1}$, the range from 0.5 to 2 $h^{-1}$ being particularly favorable.

The catalysts can be employed repeatedly for the reaction. They can be regenerated again by simple calcination in an oxidizing atmosphere, in particular in air or air/nitrogen mixtures, at temperatures between about 350° and 800° C., preferably between about 500° and 600° C.

The mixture obtained in the reaction can be separated in a conventional manner. Unreacted reactants can be distilled off and used again for the acylation reaction. The resulting isomeric acylated products can as a rule be coarsely separated by means of a distillation; they can be purified to the desired degree by further purification steps such as distillation and recrystallization.

The examples below are intended to illustrate the process according to the invention in greater detail, without it being restricted thereto

EXAMPLES

The catalytic experiments in the liquid phase were carried out in a stirred vessel. The zeolite was employed in powder form and was dried in vacuo at 250° C. for 1 h before the reaction. The reactants were employed in an equimolar ratio except in Examples 13 and 14. Some results for the liquid phase acylation of 2-methoxynaphthalene (2-MO-Np) are assembled in Table 1.

The gas phase experiments were carried out in a solid-bed flow reactor at atmospheric pressure. 2-Methoxynaphthalene was dissolved in an excess of acylating agent, and the reactant mixture was metered in in liquid form and evaporated upstream of the catalyst bed. Nitrogen was used as a carrier gas. The products were condensed downstream of the reactor after various catalyst transit times and analyzed by gas chromatography. The catalyst was employed in the form of extrudates which contained 21% by weight of $SiO_2$ as a binder. Some results are assembled in Table 2.

TABLE 1

Acylation of 2-methoxynaphthalene, liquid phase

| | | | | | Product yields[d], mol % | | Isomer ratio | | |
|---|---|---|---|---|---|---|---|---|---|
| | | | | | | | 1- | 6- | Other |
| Example | Zeolite | Acylating agent[c] | Temp. °C. | Time h | Acyl-2-MO-Np | Other | Acyl-2-MO-Np | | |
| 1 | — | $Ac_2O$ | 159 | 4.0 | 0 | 0 | | | |
| 2 | HEU-1 | AcCl | 51–70 | 13.5 | 26 | 0 | 97 | 2 | 1 |
| 3 | HEU-1 | $Ac_2O$ | 155 | 6.5 | 14 | 0 | 80 | 16 | 4 |
| 4 | HBeta | $Ac_2O$ | 154 | 2.5 | 22 | 0 | 70 | 18 | 12 |
| 5 | HBeta | $Ac_2O$/AcOH | 139 | 4.5 | 16 | 1 | 55 | 39 | 6 |
| 6 | HBeta | $Ac_2O$, add dropwise | 154 | 2.0 | 16 | 1 | 60 | 34 | 6 |
| | | | | 10.5 | 18 | 1 | 65 | 29 | 6 |
| 7 | HZSM-12[a] | $Ac_2O$, add dropwise | 158 | 6.0 | 25 | 0 | 83 | 15 | 2 |
| 8 | HZSM-12[b] | $Ac_2O$, add dropwise | 158 | 6.0 | 9 | 0 | 80 | 20 | 0 |
| 9 | HBeta | propionyl chloride | 133–122 | 3.7 | 35 | 3 | 87 | 13 | 0 |
| 10 | HBeta | propionic anhydride | 175 | 6.0 | 18 | 2 | 73 | 26 | 1 |
| 11 | HZSM-12[a] | propionic anhydride | 175 | 6.0 | 19 | 1 | 74 | 25 | 1 |
| 12 | HZSM-12[b] | propionic anhydride | 175 | 2.0 | 11 | 1 | 67 | 31 | 2 |
| 13 | HBeta | $Ac_2O$[e] add dropwise | 155 | 2.5 | 12 | 2 | 56 | 44 | 0 |
| 14 | HBeta | $Ac_2O$[f], add dropwise | 155 | 5.5 | 27 | 1 | 68 | 32 | 0 |

[a]crystallite size 0.05 μm
[b]crystallite size 0.5 μm
[c]Ac = $CH_3CO$
[d]only based on products from 2-MO-Np
[e]amount ratio 2-MO-Np:$Ac_2O$ = 1:0.5
[f]amount ratio 2-MO-Np:$Ac_2O$ = 1:3

TABLE 2

Acylation of 2-methoxynaphthalene, gas phase

| Example | Zeolite | Acylating agent[a] | mol per mol 2-MO-Np | Temp. °C. | LHSV h$^{-1}$ | Transit time h | Product yields[b], mol % | | Isomer ratio | | |
|---|---|---|---|---|---|---|---|---|---|---|---|
| | | | | | | | Acyl-2-MO-Np | Other | 1- | 6- | Other |
| | | | | | | | | | Acyl-2-MO-Np | | |
| 15 | HEU-1 | AcOH | 8 | 250 | 1 | 0.5–1 | 1 | 1 | 10 | 90 | 0 |
| 16 | HEU-1 | AcCl | 10 | 250 | 1 | 0.5–1 | 6 | 3 | 77 | 23 | 0 |
| 17 | HEU-1 | Ac$_2$O | 5 | 250 | 1 | 0.5–1 | 4 | 4 | 66 | 34 | 0 |
| 18 | HZSM-12 | propionic anhydride | 4 | 250 | 1 | 0–0.5 | 11 | 2 | 19 | 80 | 1 |
| | | | | | | 2.5–4.5 | 9 | 2 | 16 | 83 | 1 |
| 19 | HZSM-12 | propionic anhydride | 4 | 200 | 1 | 0.5–1 | 11 | 2 | 54 | 44 | 2 |
| 20 | HZSM-12 | propionic anhydride | 4 | 300 | 1 | 0.5–1 | 15 | 2 | 9 | 89 | 2 |
| 21 | HZSM-12 | propionic acid | 8 | 300 | 1 | 0.5–1 | 10 | 5 | 2 | 94 | 4 |

[a] Ac = CH$_3$CO
[b] only based on products from 2-MO-Np

We claim:

1. In a process for the reaction of a 2-naphthyl ether of the formula (I)

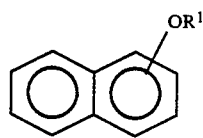

with an acylating agent of the formula R$^2$13 CO—X, in which X is Cl, Br, —OCOR$^2$, OH or C$_1$- to C$_3$-alkoxy, to give an acylated naphthyl ether of the formula

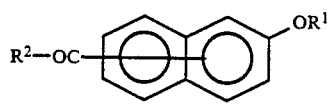

in which the group R$^2$—OC is bonded in the 1- or 6-position and R$^1$ and R$^2$ independently of one another are C$_1$- to C$_{10}$-alkyl or C$_2$- to C$_{10}$-alkenyl and carrying out the reaction in the presence of zeolite catalysts which have the formula Z.Al$_2$O$_3$xSiO$_2$ (III) in the anhydrous and template-free form, in which Z is M$^I_2$O, M$^{II}$O and/or (M$^{III}$)$_2$O$_3$, in which M$^I$ is an alkali metal atom, ammonium or a hydrogen atom, M$^{II}$ is an alkaline earth metal atom and M$^{III}$ is a rare earth metal of atomic number 57 to 71 in the periodic table of the elements, and x is a number from 4 to 4000, with the proviso that at least 50% of the negative lattice charges are compensated by protons, ammonium and/or the other metal ions mentioned under M$^{II}$ and M$^{III}$, and the pores of which are formed from at least 10 tetrahedral atoms, and carrying out the reaction at a temperature between 30° C. and 500° C., the improvement consisting essentially of:

a) in the formation of the 6-acylated naphthyl ether of formula (II) by carrying out the reaction in a gas phase at a temperature range between 150° C. and 500° C. and by using as the acylating agent a carboxylic acid or a carboxylic anhydride of the formula R$^2$—CO—X, wherein X is —OCOR$^2$ or OH, in the case of a carboxylic anhydride the reaction temperature being at or below 250° C., and b) in the formation of the 1-acylated naphthylether of formula (II) by b1) carrying out the reaction in a gas phase at a temperature range between 150° C. and 500° C. and using as the acylating agent an acid halogenide of the formula R$^2$—CO—X, wherein X is Cl or Br or by b2) carrying out the reaction in a liquid phase at a temperature range between 30° C. and 200° C. and using as the acylating agent an acid halogenide or a carboxylic anhydride of the formula R$^2$—CO—X, wherein X is Cl, Br or —OCOR$^2$.

2. The process as claimed in claim 1, wherein if Z is M$^I_2$O, at least 75% of the alkali metal atoms are replaced by hydrogen atoms, ammonium, alkaline earth metal atoms and/or rare earth metal atoms.

3. The process as claim ed in claim 2, wherein x in the formula (III) is a number from 20 to 300.

4. The process as claimed in claim 1, wherein the crystallite size of the zeolites is between about 0.01 and about 10 μm.

5. The process as claimed in claim 1, wherein the reaction is carried out in the pressure range from 0.5 to 100 bar.

6. The process as claimed in claim 1, wherein 0.1 to 20 mol of acylating agent are employed per mol of naphthyl ether.

7. The process as claimed in claim 1, wherein between 0.5 and 100% by weight of catalyst, are employed relative to the weight of reactants employed.

8. The process as claimed in claim 1, wherein the acylating agent is added slowly at reaction temperature to the naphthyl ether/catalyst suspension.

9. The process as claimed in claim 1, wherein the reaction is carried out at temperatures of about 100° to 300° C.

10. The process as claimed in claim 1, wherein the crystallite size of the zeolites is between about 0.05 and about 0.1 μm.

11. The process as claimed in claim 1, wherein the reaction is carried out in the pressure range from 1 to 10 bar.

12. The process as claimed in claim 1, wherein 0.5 to 5 mol of acylating agent are employed per mol of naphthyl ether.

13. The process as claimed in claim 1, wherein between 1 and 10% by weight of catalyst are employed relative to the weight of reactants employed.

14. The process as claimed in claim 1, wherein the reaction in the gas phase is carried out at a temperature range between 200° C. and 300° C.

15. The process as claimed in claim 1, wherein the reaction in the liquid phase is carried out at a temperature range between 120° C. and 170° C.

* * * * *

UNITED STATES PATENT AND TRADEMARK OFFICE
CERTIFICATE OF CORRECTION

PATENT NO. : 5,227,529
DATED : July 13, 1993
INVENTOR(S) : Marita Neuber, et al

It is certified that error appears in the above-indentified patent and that said Letters Patent is hereby corrected as shown below:

Col. 4, line 14, "monium" should read --alkaline earth metals or rare earth metals or for ammonium ions--

Column 7, line 29, "$R^213$ CO-X" should read --$R^2$-CO-X--

Signed and Sealed this

Twelfth Day of April, 1994

Attest:

BRUCE LEHMAN

*Attesting Officer*  *Commissioner of Patents and Trademarks*